United States Patent [19]

Behre et al.

[11] 4,369,143

[45] Jan. 18, 1983

[54] PROCESS FOR THE PREPARATION OF NAPHTHALENE-1,3,5-TRISULPHONIC ACID

[75] Inventors: Horst Behre; Heinz U. Blank, both of Odenthal; Wolfgang Schenk, Leverkusen, all of Fed. Rep. of Germany

[73] Assignee: Bayer Aktiengesellschaft, Leverkusen, Fed. Rep. of Germany

[21] Appl. No.: 287,591

[22] Filed: Jul. 28, 1981

Related U.S. Application Data

[63] Continuation of Ser. No. 106,807, Dec. 26, 1979, abandoned.

[30] Foreign Application Priority Data

Jan. 13, 1979 [DE] Fed. Rep. of Germany ....... 2901178

[51] Int. Cl.³ .......................................... C07C 143/24
[52] U.S. Cl. ................................................ 260/505 C
[58] Field of Search ..................................... 260/505 C

[56] References Cited

PUBLICATIONS

Gilbert "Sulfonation & Related Reactions" (1965), p. 89.
Ullmann's "Enzyklopadie der Technischen Chemie" 3rd ed., vol. 12, pp. 596,631.

*Primary Examiner*—Alan Siegel
*Attorney, Agent, or Firm*—Sprung, Horn, Kramer & Woods

[57] ABSTRACT

A process is provided for the preparation of naphthalene-1,3-5,-trisulphonic acid from 1,5-disulphonated naphthalene, which comprises sulphonating 1,5-disulphonated naphthalene, in the form of a mixture which has been obtained by mixing naphthalene and $SO_3$ in the presence of an inert solvent at temperatures in the range of $-40°$ to $+20°$ C., the ratio of $SO_3$ added to naphthalene added having been in the range of 2.5 to 10 mols of $SO_3$ per mol of naphthalene during the entire addition, at 60° to 110° C. in anhydrous sulphuric acid with oleum, with prior or concurrent separation of the inert solvent.

The resulting product is a known intermediate for the formation of azo dyestuffs.

9 Claims, No Drawings

PROCESS FOR THE PREPARATION OF NAPHTHALENE-1,3,5-TRISULPHONIC ACID

This is a continuation of application Ser. No. 106,807, filed Dec. 26, 1979 now abandoned.

The present invention relates to a process for the preparation of naphthalene-1,3,5-trisulphonic acid by sulphonation of a product mixture which has been obtained by reacting naphthalene with sulfur trioxide in an inert solvent.

In FIAT Final Report No. 1016, pages 42 to 44, the preparation of naphthalene-1,3,5-trisulphonic acid is described as follows:

Naphthalene is introduced at 30° to 35° C. into monohydrate (=100% strength $H_2SO_4$), 65% strength oleum being run in at the same time. The reaction mixture is kept at 50° C. for one hour, at 70° C. for one hour and at 90° C. for seven hours, until everything has dissolved. With this process the yield of naphthalene-1,3,5-trisulphonic acid is about 68%, based on the naphthalene employed. In addition, about 21% of naphthalene-1,3,6-trisulphonic acid and about 4 to 5% of naphthalene-1,3,7-trisulphonic acid are formed (see Example 6).

In Ullmann's Enzyklopädie der technischen Chemie (Encyclopaedia of Industrial Chemistry), 3rd edition, volume 12, pages 596 and 631 and in the literature cited in this publication it is stated that naphthalene-1,3,5-trisulphonic acid can be prepared by sulphonation of naphthalene-1,5-disulphonic acid with oleum. A disadvantage of this process is that the naphthalene-1,5-disulphonic acid first has to be isolated as the free acid in the form of its tetrahydrate or as the disodium salt in the form of the dihydrate. On further sulphonation to naphthalene-1,3,5-trisulphonic acid, considerable amounts of oleum are therefore required in order to bind the water of crystallisation. This results in unfavourable space-time yields and high consumption of oleum. Moreover, because of the unsatisfactory yield of the naphthalene-1,5-disulphonic acid, or the disodium salt thereof, which is isolated, the yield of naphthalene-1,3,5-trisulphonic acid, based on naphthalene, is unfavourable.

A process for the preparation of naphthalene-1,3,5-trisulphonic acid from 1,5-disulphonated naphthalene has now been found which is characterised in that 1,5-disulphonated naphthalene, in the form of a mixture which has been obtained by mixing naphthalene and $SO_3$ in the presence of an inert solvent at temperatures in the range of −40° to +20° C. the ratio of $SO_3$ added to naphthalene added having been in the range of 2.5 to 10 mols of $SO_3$ per mol of naphthalene during the entire addition, is sulphonated at 60° to 110° C. in anhydrous sulphuric acid with oleum, the inert solvent being separated off beforehand or at the same time.

The feed product for the process according to the invention can preferably be obtained by dissolving naphthalene and $SO_3$, each separately, in an inert solvent, preferably in an aliphatic chlorinated hydrocarbon with 1 to 3 C atoms, especially a chlorinated alkane such as methylene chloride, and combining the two solutions at about −10° to −5° C., a molar ratio of $SO_3$ added to naphthalene added in the range of 2.5 to 3.6 and preferably in the range of 3.0 to 3.2 being maintained during the entire addition. A sulphonation product of naphthalene forms, which separates out in solid form and contains $H_2SO_4$ and in some cases $SO_3$. The sulphonation product is obtained as a suspension in the solvent used.

This sulphonation product of naphthalene, which in the text which follows is also termed Armstrong acid anhydride or AA-AN, is a mixture of oligomeric anhydrides of naphthalene-di- and -tri-sulphonic acids with $H_2SO_4$ and in some cases $SO_3$. If the sulphonated naphthalene units present in the AA-AN are regarded formally as naphthalenesulphonic acids and the $H_2SO_4$ is regarded as $SO_3$, the AA-AN can contain, for example, 69 to 88% by weight of naphthalene-di- and -tri-sulphonic acids and 31 to 12% by weight of $SO_3$ and in general contains more than 65% by weight of naphthalene-1,5-disulphonic acid, based on the total amount of naphthalenesulphonic acids.

The mixtures preferably employed in the process according to the invention are those which contain, regarded formally, 70 to 82% by weight of naphthalene-1,5-disulphonic acid, based on the total amount of naphthalenesulphonic acids. A particularly preferred AA-AN contains: 75–80% by weight of naphthalene-1,5-disulphonic acid, 0–3% by weight of naphthalene-1,3-disulphonic acid, 5–15% by weight of naphthalene-1,6-disulphonic acid, 2–5% by weight of naphthalene-1,7-disulphonic acid, 0–10% by weight of naphthalene-1,3,5-trisulphonic acid, 0–10% by weight of naphthalene-1,3,6-trisulphonic acid, 0–1% by weight of naphthalene-1,3,7-trisulphonic acid and 0–1% by weight of naphthalene-1-sulphonic acid, in each case based on the sum of all the naphthalene derivatives and calculated as free sulphonic acids.

In addition, the AA-AN can contain very small amounts of further dinaphthylsulphones and dinaphthylsulphone-sulphonic acids, which are not identified more specifically.

The mixture of oligomeric anhydrides of naphthalene-di- and -tri-sulphonic acids with $H_2SO_4$ and in some cases $SO_3$ is obtained from the preparation as a suspension in the particular solvent used. In order to obtain naphthalene-1,3,5-trisulphonic acid from this suspension, the solid constituents of which, as mentioned above, contain in the main 1,5-disulphonated naphthalene units, the suspension is brought to temperatures in the range of 60° to 110° C. in anhydrous sulphuric acid or oleum. If this mixture contains between 3 and 5 mols of $SO_3$ per mol of naphthalene originally employed, it is not necessary, for example, to employ additional $SO_3$ or water or dilute sulphuric acid.

The inert solvent can be removed at any desired time, preferably before naphthalene-1,3,5-trisulphonic acid starts to form in significant amounts.

If more than 5 mols of $SO_3$ per mol of naphthalene originally employed are present in the reaction mixture which contains the Armstrong acid anhydride and anhydrous sulphuric acid or oleum, it is advantageous to add, for example, water or dilute sulphuric acid until the molar ratio of $SO_3$ to naphthalene originally employed is in the range of 3:1 to 5:1. Correspondingly, it is advantageous to add, for example, $SO_3$ or oleum if less than 3 mols of $SO_3$ per mol of naphthalene originally employed are present in the abovementioned reaction mixture.

If AS-AN which has been obtained by the procedure described above as being preferred is employed in the process according to the invention, it is generally advantageous if $SO_3$ is added to the sulphonation mixture for the formation of naphthalene-1,3,5-trisulphonic acid. The $SO_3$ can be employed, for example, as such or in the form of oleum. The procedure can also be to introduce the feed mixture into oleum to form the naphthalene-1,3,5-trisulphonic acid. The amount of $SO_3$ added is generally adjusted depending on the $SO_3$ content of the AA-AN which is used. For example, 0 to 1.0 mol of $SO_3$ and preferably 0.1 to 0.8 mol of $SO_3$, for example in the form of oleum, can be added per mol of naphthalene in the form of the 1,5-disulphonated naphthalene (AA-AN). Oleum with a $SO_3$ content of 5 to 100% by weight and especially the commercially available approximately 65% strength oleum is, for example, suitable for this purpose.

The temperature for the formation of the naphthalene-1,3,5-trisulphonic acid is adjusted in the range of 60° to 110° C. Temperatures in the range of 80° to 100° C. and especially of 85° to 95° C. are preferred.

The reaction times for the formation of the naphthalene-1,3,5-trisulphonic acid essentially depend on the reaction temperature and on the $SO_3$ concentration in the reaction mixture. At relatively high temperatures and with relatively high $SO_3$ concentrations, a relatively short reaction time can be chosen and at relatively low temperatures and with relatively low $SO_3$ concentrations a longer reaction time can be chosen. Preferably, the reaction time is in the range between 5 and 10 hours and especially 6 to 8 hours.

The process for the formation of naphthalene-1,3,5-trisulphonic acid can be carried out in various variants. Three variants are indicated in detail below:

Variant 1

The inert solvent is removed from the feed product before it is mixed with anhydrous sulphuric acid and optionally $SO_3$. This is effected, for example, by filtration with subsequent drying or only by drying. The solvent separated off in this way can be re-used for the sulphonation of naphthalene to AA-AN. The dry mixture (AA-AN) is then added to anhydrous sulphuric acid, which has been initially introduced. Thus, 1 to 10 mols of monohydrate (=100% strength $H_2SO_4$) and preferably 2 to 4 mols of monohydrate per mole of naphthalene in the form of AA-AN are initially introduced. $SO_3$ preferably in the form of oleum, is then optionally metered in. The introduction of AA-AN and the metering in of oleum is effected simultaneously, alternately in small portions or successively. Metering is carried out at room temperature or preferably at elevated temperature, for example at 30° to 90° C. The metering times are preferably so chosen that the reaction mixture remains easily stirrable and pumpable.

This is generally the case with metering times in the range of 15 minutes to 2 hours. After metering has ended, the sulphonation to naphthalene-1,3,5-trisulphonic acid is carried out, preferably at 85° to 95° C., in the course of 5 to 10 hours and preferably 6 to 8 hours.

Variant 2

Anhydrous sulphuric acid and a portion of completely reacted sulphonation mixture from a preceding batch are first added, successively, simultaneously or after prior mixing, to the feed product. Two liquid phases form; these are an acid phase and a solvent phase. It is possible, for example, to add anhydrous sulphuric acid in an amount such as is indicated in variant 1 and, in addition, about 10 to 70% by weight of the crude completely reacted sulphonation mixture from a preceding batch. It is advantageous if the acid phase which forms corresponds to about 50 to 250% by weight of the solvent phase. The bulk of the inert solvent, for example about 80 to 95%, is then separated off by decanting. The decantation residue is then freed from the residual inert solvent by distillation, for example by distillation in vacuo. Decanting is preferably carried out at about 15° to 25° C. and the residual solvent is preferably distilled off at 10° to 30° C. and under 10 to 100 mm Hg. The solvent separated off in this way can be re-used in the sulphonation of naphthalene to AA-AN. The formation of naphthalene-1,3,5-trisulphonic acid is then effected in the course of 5 to 10 hours by adjusting the temperature to a temperature in the range of 60° to 110° C. and, if appropriate, after adding oleum. After the sulphonation has ended, between about 10 and 70% by weight of the crude, completely reacted sulphonation mixture are recycled into the phase separation stage.

Variant 3

The procedure is as in variant 1 or 2, except that the inert solvent is separated off, for example by distillation, only when the temperature has been adjusted to within the range of 60° to 110° C.

Particularly preferentially, the procedure according to variant 1 or variant 2 is followed. These variants can also be carried out continuously without difficulty.

According to the process of the invention, naphthalene-1,3,5-trisulphonic acid is obtained in yields of about 83%, based on naphthalene, that is to say in considerably higher yields than according to the cited prior art. The completely reacted sulphonation mixture obtained by the process according to the invention contains, in addition to naphthalene-1,3,5-trisulphonic acid, about 15% of naphthalene-1,3,6-trisulphonic acid and small amounts of naphthalene-1,3,7-trisulphonic acid and naphthalene-1,3,5,7-tetrasulphonic acid (in each case based on naphthalene employed). Compared with the processes known hitherto, high space-time yields are obtained and the consumption of auxiliaries, for example monohydrate, is considerably reduced with the process according to the invention.

The product obtained after carrying out the process according to the invention can be further used in any desired manner without isolating the naphthalene-1,3,5-trisulphonic acid. For example it is suitable for the preparation of the important dyestuff intermediate products naphthamine tri-acid K (melanic acid) and K-acid, in which case the steps comprising nitration, chalking, reduction and precipitation of naphthamine tri-acid K and conversion of the naphthamine tri-acid K to K-acid can be carried out in accordance with FIAT Final Report No. 1016, pages 42 to 44 or in another way.

EXAMPLES

EXAMPLE 1

350 g of 100% strength by weight $H_2SO_4$ are initially introduced into a 2 l four-necked flask fitted with a metering screw, a metering dropping funnel, an internal thermometer and a sickle stirrer. 369 g of AA-AN are added in the course of about 30 minutes via the metering screw, whilst stirring; this product (AA-AN) had been obtained as follows:

128 g (1.0 mol) of naphthalene are dissolved in 640 g of methylene chloride and at the same time 243 g of liquid $SO_3$ are dissolved in 950 g of methylene chloride. The two solutions are allowed to run simultaneously into 100 g of methylene chloride, which has been initially introduced, at such a rate that it is possible to keep the temperature between −5° and −10° C. After mixing is complete, the reaction mixture is kept at −5° to −10° C. for 1.5 hours and then evaporated to dryness in vacuo. Regarded formally, the product thus obtained was the following composition: 59.6% by weight of naphthalene-1,5-disulphonic acid, 0.2% by weight of naphthalene-1,3-disulphonic acid, 5.2% by weight of naphthalene-1,6-disulphonic acid, 2.2% by weight of naphthalene-1,7-disulphonic acid, 2.5% by weight of naphthalene-1,3,5-trisulphonic acid, 5.8% by weight of naphthalene-1,3,6-trisulphonic acid, 0.5% by weight of naphthalene-1,3,7-trisulphonic acid and 24.0% by weight of $SO_3$.

During the metering in of the AA-AN, the reaction mixture is warmed to 70° C. 42 g of 65% oleum are then added dropwise via the metering dropping funnel and the reaction mixture is stirred at 90° C. for 7 hours.

The following contents are determined by high-pressure liquid chromatography in the reaction mixture obtained after the sulphonation reaction:
Naphthalene-1,3,5-trisulphonic acid: 40.2% by weight
Naphthalene-1,3,6-trisulphonic acid: 7.4% by weight
Naphthalene-1,3,7-trisulphonic acid: 1.4% by weight
Naphthalene-1,3,5,7-tetrasulphonic acid: 0.2% by weight
Sulphuric acid: about 51.0% by weight The yield of naphthalene-1,3,5-trisulphonic acid is 82%, based on naphthalene.

The resulting mixture of naphthalene-trisulphonic acid isomers is further processed, without intermediate isolation of the naphthalene-1,3,5-trisulphonic acid by nitration, chalking and reduction in accordance with FIAT Final Report No. 1016, pages 42 to 44, to give naphthamine-tri-acid K.

EXAMPLE 2

A reaction which is carried out as in Example 1 and in which a sulphonation product is employed which was obtained as in Example 1, but for which 264 g of $SO_3$ are dissolved in 1.025 g of methylene chloride and which, regarded formally, has the following composition: 56.0% by weight of naphthalene-1,5-disulphonic acid, 9.1% by weight of naphthalene-1,3,5-trisulphonic acid, 16.2% by weight of further naphthalene-disulphonic acids and naphthalene-trisulphonic acids and 19.0% by weight of $SO_3$, and in which the reaction mixture is stirred for 10 hours at 85° C. after adding 42 g of 65% oleum, yields naphthalene-1,3,5-trisulphonic acid in a yield of 83%, based on naphthalene.

EXAMPLE 3

The procedure is as in Example 1 except that the reaction mixture is stirred for 12 hours at 80° C. after adding 42 g of 65% oleum. The yield of naphthalene-1,3,5-trisulphonic acid was 80%, based on naphthalene.

EXAMPLE 4

A suspension of 369 g of AA-AN in 900 g of methylene chloride, which has the composition indicated in Example 1, is initially introduced into a 3 l three-necked flask fitted with a dropping funnel, an internal thermometer and a sickle stirrer.

194 g of crude sulphonation reaction mixture (recycled from the previous sulphonation batch) and 350 g of 100% $H_2SO_4$ are initially introduced into a separate flask and mixed. The mixture from the separate flask is now added at 20° C. to the suspension of AA-AN and methylene chloride and the whole is stirred slowly until the methylene chloride separats out clearly in the upper layer, after which it is sucked off (decanted off). The methylene chloride which is thus obtained and which amounts to about 725 g is recycled, without working up, into the sulphonation of naphthalene. The remaining 175 g of methylene chloride are distilled off at 10° to 30° C. and under 20 mm Hg.

The trisulphonation is effected by adding 42 g of 65% oleum to the slurry obtained as the distillation residue and warming the reaction mixture at 95° C. for 4 hours. The yield of naphthalene-1,3,5-trisulphonic acid is 82%, based on naphthalene. The content of organically bonded chlorine in the sulphonation mixture is less than 0.2%.

About one quarter of the resulting reaction mixture is recycled into the two-phase separation stage and the remaining three quarters of the mixture are further processed in accordance with FIAT Final Report 1016, pages 42 to 44, to give naphthamine tri-acid K.

EXAMPLE 5

The procedure is as in Example 4 except that 388 g of crude sulphonation reaction mixture and 350 g of 100% $H_2SO_4$ are initially introduced into the separate flask and mixed. For the trisulphonation, the reaction mixture is stirred at 100° C. for 4 hours.

85% of the methylene chloride employed is recovered by decanting and 15% was recovered by distillation. The yield of naphthalene-1,3,5-trisulphonic acid is 81%, based on naphthalene.

EXAMPLE 6

(corresponding to FIAT Final Report No. 1016, pages 42 to 44)

225 g of 100% strength $H_2SO_4$ are initially introduced into an apparatus as described in Example 1. 128 g of naphthalene are metered in in the course of about 1 hour at 30° to 35° C. and 410 g of 65% oleum are run in at the same time. The reaction mixture is heated to 50° C. and kept at 50° C. for one hour, at 70° C. for one hour and at 90° C. for seven hours.

The following contents are determined, by high-pressure liquid chromatography, in the reaction mixture obtained after the sulphonation reaction:
Naphthalene-1,3,5-trisulphonic acid: 33.0% by weight
Naphthalene-1,3,6-trisulphonic acid: 10.3% by weight
Naphthalene-1,3,7-trisulphonic acid: 2.1% by weight
Naphthalene-1,3,5,7-tetrasulphonic acid: 0.3% by weight
Sulphuric acid: about 54% by weight The yield of naphthalene-1,3,5-trisulphonic acid is 68%, based on naphthalene.

What is claimed is:

1. Process for the preparation of naphthalene-1,3,5-trisulphonic acid from 1,5-disulphonated naphthalene, which comprises using 1,5-disulphonated naphthalene in the form of a reaction mixture which has been obtained by mixing naphthalene and $SO_3$ in the presence of methylene chloride at temperatures in the range of −10° to −5° C., the ratio of the $SO_3$ added to the naphthalene added having been in the range of 2.5 to 10 mols of $SO_3$ per mol of naphthalene during the entire addition, and sulfonating this reaction mixture at 60° to 110° C. in anhydrous sulphuric acid with oleum, with prior or concurrent separation of the methylene chloride.

2. Process according to claim 1, wherein in the reaction mixture consisting of the mixture containing 1,5-disulphonated naphthalene and of anhydrous sulphuric acid and oleum, the molar ratio of $SO_3$ to naphthalene originally employed is adjusted to 3:1 to 5:1 by adding water, dilute sulphuric acid or oleum.

3. Process according to claim 1 or 2, wherein the starting material used is 1,5-disulphonated naphthalene which has been obtained by dissolving naphthalene and $SO_3$, each separately, in an methylene chloride, combining the two solutions at $-10°$ to $-5°$ C. and maintaining a molar ratio of $SO_3$ added to naphthalene added in the range of 2.5 to 3.6 during the entire addition.

4. Process according to claim 1 or 2, wherein no additional $SO_3$ is employed in the sulphonation reaction for the formation of naphthalene-1,3,5-trisulphonic acid.

5. Process according to claim 3, wherein 0.1 to 0.8 mol of $SO_3$ per mol of naphthalene in the form of the 1,5-disulphonated naphthalene is added in the sulphonation reaction for the formation of naphthalene-1,3,5-trisulphonic acid.

6. Process according to claim 5, wherein $SO_3$ is added in the form of oleum.

7. Process according to claim 1, wherein for the formation of naphthalene-1,3,5-trisulphonic acid, the temperature is adjusted to a temperature in the range of 80° to 100° C.

8. Process according to claim 1, wherein the methylene chloride is removed from the feed product before it is mixed with anhydrous sulphuric acid and optionally $SO_3$.

9. Process according to claim 7, where anhydrous sulphuric acid and a portion of completely reacted sulphonation mixture are first added to the feed product, the bulk of the methylene chloride is then separated off by decanting and the residual inert solvent in then separated off by distillation.

* * * * *